US011866488B2

(12) United States Patent
Lynes et al.

(10) Patent No.: US 11,866,488 B2
(45) Date of Patent: Jan. 9, 2024

(54) COMPOSITIONS COMPRISING AN ANTI-METALLOTHIONEIN ANTIBODY AND A PANCREATIC CELL TARGETING MOIETY

(71) Applicants: UNIVERSITY OF CONNECTICUT, Farmington, CT (US); JOSLIN DIABETES CENTER, INC., Boston, MA (US)

(72) Inventors: Michael A. Lynes, Farmington, CT (US); Yu-Hua Tseng, Boston, MA (US); Matthew D. Lynes, Boston, MA (US)

(73) Assignees: UNIVERSITY OF CONNECTICUT, Farmington, CT (US); JOSLIN DIABETES CENTER, INC., Boston, MA (US)

(*) Notice: Subject to any disclaimer, the term of this patent is extended or adjusted under 35 U.S.C. 154(b) by 0 days.

(21) Appl. No.: 16/961,327

(22) PCT Filed: Jan. 17, 2019

(86) PCT No.: PCT/US2019/013934
§ 371 (c)(1),
(2) Date: Jul. 10, 2020

(87) PCT Pub. No.: WO2019/143767
PCT Pub. Date: Jul. 25, 2019

(65) Prior Publication Data
US 2020/0369757 A1  Nov. 26, 2020

Related U.S. Application Data

(60) Provisional application No. 62/618,332, filed on Jan. 17, 2018.

(51) Int. Cl.
C07K 16/40 (2006.01)
C07K 16/18 (2006.01)
A61P 3/10 (2006.01)
A61K 45/06 (2006.01)
A61K 39/00 (2006.01)

(52) U.S. Cl.
CPC ............. *C07K 16/18* (2013.01); *A61P 3/10* (2018.01); *A61K 45/06* (2013.01); *A61K 2039/505* (2013.01); *C07K 2317/24* (2013.01); *C07K 2319/33* (2013.01)

(58) Field of Classification Search
None
See application file for complete search history.

(56) References Cited

U.S. PATENT DOCUMENTS

| 8,962,598 B2 | 2/2015 | Pettersson | |
| 2003/0007973 A1* | 1/2003 | Lynes | C07K 16/18 |
| | | | 424/146.1 |
| 2012/0244080 A1* | 9/2012 | Liu | A61K 38/26 |
| | | | 435/7.1 |
| 2014/0141009 A1 | 5/2014 | De Vos et al. | |
| 2016/0046940 A1 | 2/2016 | Bhat et al. | |
| 2017/0014379 A1 | 1/2017 | Turkyilmaz et al. | |
| 2017/0143798 A1* | 5/2017 | McGuckin | C07K 19/00 |

FOREIGN PATENT DOCUMENTS

| WO | 2007/012188 | 2/2007 |
| WO | 2012/050500 | 4/2012 |
| WO | 2013/007678 | 1/2013 |
| WO | 2014/172606 | 10/2014 |
| WO | 2014/172606 A1 | 10/2014 |
| WO | 2016022753 A | 2/2016 |

OTHER PUBLICATIONS

Li et al. Diabetes 55: 1592-1604, 2006.*
Chen et al. (PLos ONE 10(9): e0137583, doi:10.1371/journal.pone.0137583, 2015).*
De Lisle et al. Am. J. Physiol. 271 (Cell Physiol. 40): C1103-C1110, 1996.*
Thirumoorthy et al. (World J. Surg. Oncol. 9:54, 2011 (pp. 1-7).*
Lynes et al. (Exp. Biol. Med. 231: 1548-1554, 2006).*
Bensellam et al. Diabetologia 62: 2273-2286, 2019.*
Canpolat et al. (Toxicol. Sci. 62: 61-70, 2001).*
Canpolat, Emel et al. "In Vivo Manipulation of Endogenous Metallothionein with a Monoclonal Antibody Enhances aT-Dependent Humoral Immune Response" Toxicological Sciences (2001) vol. 62(1), pp. 61-70.
Naka, et al., Nov. 2016. Contributions of *Streptococcus* mutans Cnm and PA antigens to aggravation of non-alcoholic streatohepatitis in mice. Sci Rep, 6: 36886.
Lu, et al., Jan. 2014. "Construction of a novel liver-targeting fusion interferon by incorporation of a plasmodium region I-plus peptide." Biomed Res Int, Epub vol. 2014: article 2612631.
Harding, et al., May 2006. "Population impact of strategies for indetifying groups at high risk of type 2 diabetes." Prev Med, 42(5): 364-8.
Katsarou, et al., May 2017. "Type 1 diabetes mellitus." Nat Rev Dis Primers, vol. 3, article 17016.
Cai, "Metallothionein As an Adaptive Protein Prevents Diabetes and Its Toxicity," Nonlinearity in Biology, Toxicology, and Medicine, 2:89-103 (2004).
Tuncdemir, et al., (Aug. 2017) "Investigation of lipid peroxidation and antiapoptotic effects of zinc aganist liver damage in diabetic rats," Hum Exp Toxicol 36(8): 813-822.

(Continued)

*Primary Examiner* — Christine J Saoud
(74) *Attorney, Agent, or Firm* — MCDONNELL BOEHNEN HULBERT & BERGHOFF LLP

(57) ABSTRACT

Disclosed herein are compositions including an inhibitor of extracellular human metallothionein (MT) and a pancreatic targeting moiety linked to the inhibitor of extracellular human MT.

10 Claims, 10 Drawing Sheets

Specification includes a Sequence Listing.

(56) References Cited

OTHER PUBLICATIONS

Haynes, et al., (Oct. 2012) "Metallothionein 2a gene expression is increased in subcutaneous adipose tissue of type 2 diabetic patients," Mol Genet Metab 108(1):90-94.

Gregg, et al., "IL-10 diminish CTLA-4 expression on islet-resident T cells and sustains their activation rather than tolerance," J. Immunol., 2005, vol. 174, pp. 662-670.

* cited by examiner

COMPOSITIONS COMPRISING AN ANTI-METALLOTHIONEIN ANTIBODY AND A PANCREATIC CELL TARGETING MOIETY

CROSS REFERENCE

This application is a U.S. national phase of International Application No. PCT/US2019/013934, filed on Jan. 17, 2019, which claims priority to U.S. Provisional Application No. 62/618,332, filed Jan. 17, 2018, both of which are incorporated by reference herein in their entirety.

SEQUENCE LISTING STATEMENT

A computer readable form of the Sequence Listing is filed with this application by electronic submission and is incorporated into this application by reference in its entirety. The Sequence Listing is contained in the file created on Jul. 26, 2022 having the file name "17-1682-PCT_SeqList.txt" and is 9784 bytes in size.

BACKGROUND

Diabetes is most often treated with insulin replacement. There is research being done to replace the islets that are damaged in diabetes, but unless the inflammatory processes that damage the islet producing insulin is arrested, islet transplants or stem cell repopulation of the islets in the pancreas will be short-lived treatments. Similarly, current methods for treating hepatitis and/or inflammatory liver disease are inadequate.

SUMMARY

In a first aspect, the disclosure provides methods for treating or limiting development of a disorder selected from the group consisting of diabetes, pre-diabetes, impaired glucose tolerance, hepatitis, and/or inflammatory liver disease, comprising administering to a subject with the disorder or at risk of the disorder a therapeutically effective amount of a composition comprising an inhibitor of extracellular human metallothionein (MT) to treat or limit development of the disorder. In one embodiment, the subject has diabetes or is at risk of developing diabetes, and the method serves to treat or limit development of diabetes. In another embodiment, the subject is at risk of type 1 diabetes, and the method serves to limit development of type I diabetes in the subject; in one such embodiment, the subject may have one or more of the risk factors for type 1 diabetes, including but not limited to a parent or sibling with type 1 diabetes, a pancreatic tumor, pancreatitis, pancreatic islet cell autoantibodies, insulin autoantibodies, glutamic acid decarboxylase autoantibodies (GADA), insulinoma-associated (IA-2) autoantibodies, zinc transporter autoantibodies (ZnT8), variants of the IDDM1 gene selected from the group consisting of DRB1 0401, DRB1 0402, DRB1 0405, DQA 0301, DQB1 0302 and DQB1 0201; polyuria, polydipsia, dry mouth, polyphagia, fatigue, or weight loss.

In another embodiment, the subject has type 1 diabetes, and the method serves to treat type I diabetes in the subject; in one such embodiment the treating may comprise one or more of reducing frequency of need for insulin injection; slowing development or progression of type 1 diabetes complications in the subject including but not limited to destruction of pancreatic beta cells, hyperglycemia, hypoglycemia, polyuria, polyphagia, polydipsia, weight loss, blurred vision, fatigue, decreased wound healing capability, urinary tract infections, sexual dysfunction, dry mouth, diabetic ketoacidosis, cardiovascular disease, diabetic nephropathy, diabetic neuropathy, diabetic retinopathy, stroke, kidney failure, and foot ulcers; and delaying need for a pancreatic or pancreatic islet cell transplant.

In another embodiment, the subject is at risk of type 2 diabetes, and the method serves to limit development of type 2 diabetes in the subject; in one such embodiment, the subject may have one or more risk factors for type 2 diabetes, including but not limited to obesity, smoking, a sedentary lifestyle, a parent or sibling with type 2 diabetes, pre-diabetes, a parent or sibling with pre-diabetes, poor eating habits (ex: too much fat, not enough fiber, too many simple carbohydrates, etc.), age 50 or older, high blood pressure, high cholesterol, testosterone deficiency, metallothionein 1 A (MT1A) rs8052394 locus (G alteration) single nucleotide polymorphism, and a history of gestational diabetes.

In another embodiment, the subject has type 2 diabetes, and the method serves to treat type 2 diabetes in the subject; in one such embodiment, the treating may comprise limiting one or more of type 2 diabetic complications, including but not limited to hyperglycemia, hypoglycemia, insulin resistance, diabetic nephropathy, diabetic neuropathy, diabetic retinopathy, proteinuria, impaired glomerular clearance, diabetic circulatory disorders, kidney failure, cardiovascular disease, polyuria, polydipsia, weight loss, stroke, and reducing frequency of need for insulin or other therapy.

In a further embodiment, the subject has pre-diabetes, and the method serves to treat pre-diabetes in the subject; in one such embodiment, the treating may comprise limiting or slowing progression of one or more complications of pre-diabetes, including but not limited to type 2 diabetes, hyperglycemia, insulin resistance, and/or cardiovascular disease.

In one embodiment, the subject has impaired glucose intolerance, and the method serves to treat impaired glucose tolerance in the subject; in one such embodiment, the treating may comprise limiting or slowing progression of one or more complications of impaired glucose tolerance, including but not limited to type 2 diabetes, hyperglycemia, insulin resistance, and/or cardiovascular disease.

In a further embodiment, the subject has hepatitis, and the method serves to treat hepatitis in the subject; in one such embodiment, the treating may comprise limiting or slowing progression of one or more complications of hepatitis, including but not limited to yellow discoloration of the skin and/or whites of the eyes, poor appetite, vomiting, fatigue, abdominal pain, diarrhea, acute liver failure, scarring of the liver, liver failure, and liver cancer.

In another embodiment, the subject has an inflammatory liver disease, and the method serves to treat the inflammatory liver disease in the subject. In one such embodiment, the inflammatory liver disease may be selected from the group consisting of nonalcoholic steatohepatitis (NASH) and/or non-alcoholic fatty liver disease (NAFLD). In another such embodiment, the treating may comprise limiting or slowing progression of one or more complications of inflammatory liver disease including but not limited to fatigue, malaise, hepatic fibrosis, hepatic cancer, and/or cirrhosis of the liver.

In one embodiment, the inhibitor of extracellular human MT may comprise an anti-MT antibody or an antigen-binding fragment thereof and/or an aptamer which specifically binds to extracellular human MT. In one such embodiment, the inhibitor of extracellular human MT comprises an anti-MT antibody or an antigen-binding fragment thereof, including but not limited to a monoclonal antibody or an antigen binding fragment thereof, and a humanized anti-MT antibody, or an antigen binding fragment thereof.

In another embodiment, the inhibitor of extracellular human MT is linked to a pancreatic or heptic cell targeting moiety. In one such embodiment, the pancreatic cell targeting moiety may comprise one or more peptides or other moieties that preferentially bind pancreatic β cells, selected from the group consisting of glucagon-like peptide-1 (GLP-1), glucagon-like peptide-2 (GLP-2), peptide YY (PYY), neuropeptide Y (NPY), pancreatic peptide (PPY), and exendin-4. In another embodiment, the heptic cell targeting moiety may include, but is not limited to, circumsporozoite protein (CSP), CSP region I, CSP region I-plus, lactosaminated human serum albumin, glycosylated lipoprotein, and/or arabinogalactan.

In one embodiment, the subject is a mammal, including but not limited to a human subject.

In another aspect, the disclosure provides compositions, comprising:
  (a) an inhibitor of extracellular human metallothionein (MT); and
  (b) a pancreatic or hepatic cell targeting moiety linked to the inhibitor of extracellular human MT.

In one embodiment, the inhibitor comprises an anti-metallothionein antibody or a fragment thereof which specifically binds to human metallothionein (MT), including but not limited to a monoclonal antibody and/or a humanized antibody, or antigen binding fragments thereof. In another embodiment, the cell targeting moiety is a pancreatic cell targeting moiety, such as one selected from the group consisting of glucagon-like peptide-1 (GLP-1), glucagon-like peptide-2 (GLP-2), peptide YY (PYY), neuropeptide Y (NPY), pancreatic peptide (PPY), and exendin-4. In another embodiment, cell targeting moiety is a heptic cell targeting moiety that may include, but is not limited to, circumsporozoite protein (CSP), CSP region I, CSP region I-plus, lactosaminated human serum albumin, glycosylated lipoprotein, and/or arabinogalactan.

In one embodiment, the composition comprises a recombinant polypeptide. In other aspects, the disclosure provides recombinant nucleic acids encoding the recombinant polypeptide, recombinant expression vectors comprising the recombinant nucleic acids, recombinant host cells comprising the recombinant expression vectors, and pharmaceutical compositions comprising (a) the compositions, recombinant nucleic acids, recombinant expression vectors, or the recombinant host cells of the disclosure; and (b) a pharmaceutically acceptable carrier.

In another aspect, the disclosure provides uses of the compositions, recombinant nucleic acids, recombinant host cells comprising the recombinant expression vectors, and pharmaceutical compositions comprising the compositions, recombinant nucleic acids, recombinant expression vectors, recombinant host cells of the disclosure, or the pharmaceutical compositions of any embodiment or combination of embodiments disclosed herein to treat or limit development of a disorder selected from the group consisting of diabetes, pre-diabetes, impaired glucose tolerance, hepatitis, and/or inflammatory liver disease.

In another embodiment of the methods of the disclosure, the inhibitor of extracellular human MT comprises the compositions, recombinant nucleic acids, recombinant host cells comprising the recombinant expression vectors, and pharmaceutical compositions comprising the compositions, recombinant nucleic acids, recombinant expression vectors, recombinant host cells of the disclosure, or the pharmaceutical compositions of any embodiment or combination of embodiments disclosed herein.

DETAILED DESCRIPTION

Figure 1:
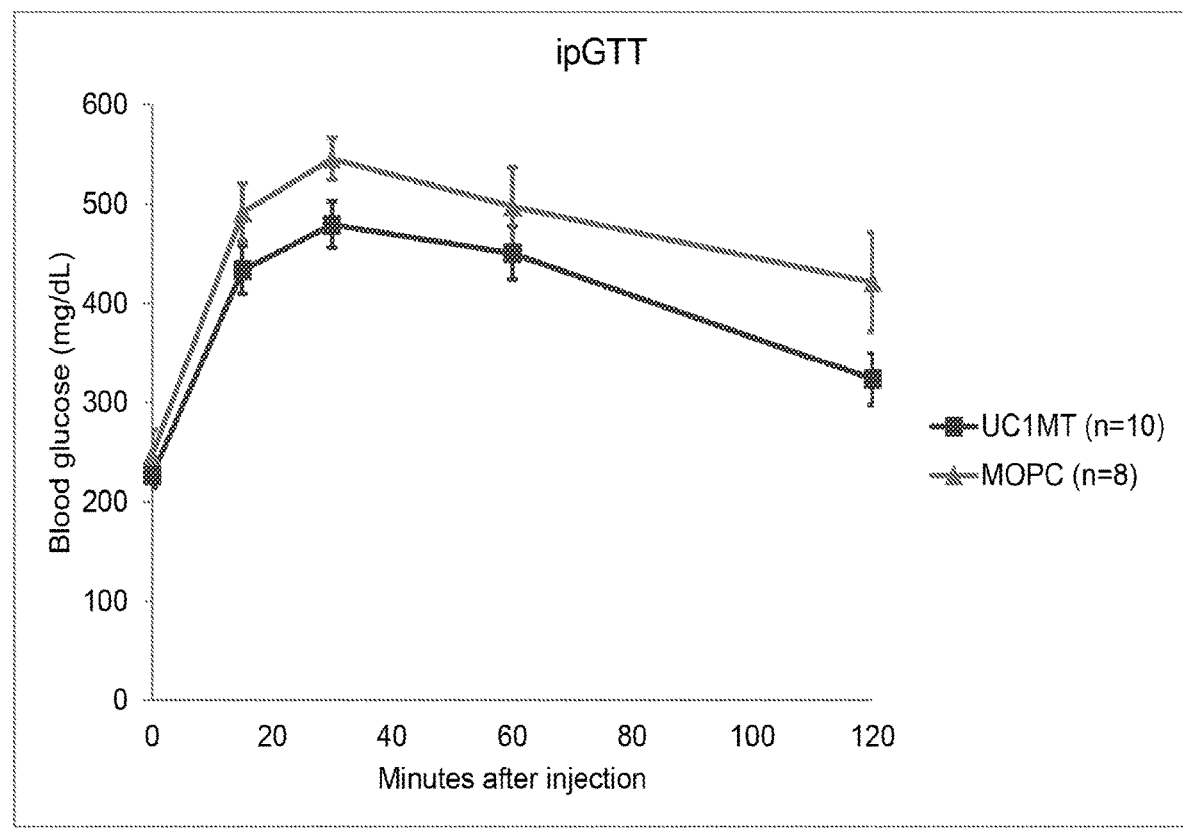
FIG. 1. Graph showing the results of glucose tolerance testing of mice injected with glucose intraperitoneally at the end of the course of treatment with MOPC21 or UC1MT.

As used herein, the singular forms "a", "an" and "the" include plural referents unless the context clearly dictates otherwise. "And" as used herein is interchangeably used with "or" unless expressly stated otherwise.

All embodiments of any aspect of the disclosure can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application. The compositions and methods for their use can "comprise," "consist essentially of," or "consist of" any of the ingredients or steps disclosed throughout the specification.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

In one aspect, the disclosure provides methods for treating or limiting development of a disorder selected from the group consisting of diabetes, pre-diabetes, impaired glucose tolerance, hepatitis, and/or inflammatory liver disease, comprising administering to a subject with the disorder or at risk of the disorder a therapeutically effective amount of a composition comprising an inhibitor of extracellular human metallothionein (MT) to treat or limit development of the disorder.

As disclosed in the examples that follow, inhibitors of extracellular human MT. surprisingly can be used to treat or limit development of diabetes, pre-diabetes, impaired glucose tolerance, hepatitis, and/or inflammatory liver disease.

As used herein, a "therapeutically effective amount" refers to an amount of the composition that is effective for treating and/or limiting the relevant disorder.

As used herein, human metallothionein means any of the 18 isoforms and sub-isoforms of metallothionein that have been identified in humans and are grouped as MT1 to MT4. Where MT3 and MT4 are selectively expressed, MT1 and MT2 are highly inducible in many cell types and can be released from cells (Lynes et al. 2006; Laukens et al. 2009). The inhibitors of the present disclosure specifically target or bind to the released metallothioneins Exemplary such isoforms include, but are not limited to:

```
Human MT1-A:
                                            (SEQ ID NO: 1)
MDPNCSCATG GSCTCTGSCK CKECKCTSCK KSCCSCCPMS

CAKCAQGCIC KGASEKCSCC A

Human MT1-B
                                            (SEQ ID NO: 2)
MDPNCSCTTG GSCACAGSCK CKECKCTSCK KCCCSCCPVG

CAKCAQGCVC KGSSEKCRCC A

Human MT1-E
                                            (SEQ ID NO: 3)
MDPNCSCATG GSCTCAGSCK CKECKCTSCK KSCCSCCPVG

CAKCAQGCVC KGASEKCSCC A

Human MT1_F
                                            (SEQ ID NO: 4)
MDPNCSCAAG VSCTCAGSCK CKECKCTSCK KSCCSCCPVG

CSKCAQGCVC KGASEKCSCC D

Human MT1-G:
                                            (SEQ ID NO: 5)
MDPNCSCAAA GVSCTCASSC KCKECKCTSC KKSCCSCCPV

GCAKCAQGCI CKGASEKCSC CA

Human MT2:
                                            (SEQ ID NO: 6)
MDPNCSCAAG DSCTCAGSCK CKECKCTSCK KSCCSCCPVG

CAKCAQGCIC KGASDKCSCC A
```

```
-continued
Human MT3:
                                            (SEQ ID NO: 7)
MDPETCPCPS GGSCTCADSC KCEGCKCTSC KKSCCSCCPA

ECEKCAKDCV CKGGEAAEAE AEKCSCCQ

Human MT-4
                                            (SEQ ID NO: 8)
MDPRECVCMS GGICMCGDNC KCTTCNCKTY WKSCCPCCPP

GCAKCARGCI CKGGSDKCSC CP
```

In one embodiment, the inhibitors of the present disclosure specifically target or bind to MT1 and/or MT2 released from cells.

The terms "specifically" or "selectively" binding to metallothionein refer to a binding reaction that is determinative of the presence of a metallothionein in a heterogeneous population of proteins and other biologics. Thus, under designated immunoassay or other conditions, the specified antibodies or aptamers of the present invention bind to a metallothionein at least two times the background and do not substantially bind in a significant amount to proteins other than metallothioneins present in the sample. Specific binding to an antibody or aptamer under such conditions may thus involve use of an inhibitor selected from the group consisting of an antibody or aptamer that is selected for its specificity to a metallothionein.

As used herein, "antibody" includes an immunoglobulin molecule immunologically reactive with human MT (preferably selective for human MT, or selective for a one or more human MT isoforms) or fragments thereof, and includes monoclonal antibodies. Various isotypes of antibodies exist, for example IgG1, IgG2, IgG3, IgG4, and other Ig, e.g., IgM, IgA, IgE isotypes. The term also includes genetically engineered forms such as chimeric antibodies (e.g., humanized murine antibodies) and heteroconjugate antibodies (e.g., bispecific antibodies), fully humanized antibodies, and human antibodies. As used throughout the application, the term "antibody" includes fragments with antigen-binding capability (e.g., Fab', F(ab')2, Fab, Fv and rIgG. See also, Pierce Catalog and Handbook, 1994-1995 (Pierce Chemical Co., Rockford, IL). See also, e.g., Kuby, J., Immunology, 3rd Ed., W.H. Freeman & Co., New York (1998). The term also refers to recombinant single chain Fv fragments (scFv). The term antibody also includes bivalent or bispecific molecules, diabodies, triabodies, and tetrabodies. Bivalent and bispecific molecules are described in, e.g., Kostelny et al., (1992) *J Immunol* 148:1547, Pack and Pluckthun (1992) *Biochemistry* 31:1579, Hollinger et al., 1993, supra, Gruber et al. (1994) *J Immunol:* 5368, Zhu et al. (1997) *Protein Sci* 6:781, Hu et al. (1996) *Cancer Res.* 56:3055, Adams et al. (1993) *Cancer Res.* 53:4026, and McCartney, et al. (1995) *Protein Eng.* 8:301. The antibodies may comprise heterobifunctional antibodies, for example, that might stabilize the MT in a particular location by way of the other arm of the antibody binding to a tissue specific determinant while the anti-MT arm blocks MT function. In one embodiment, the antibody comprises a monoclonal antibody. The examples demonstrate the methods of the disclosure using the exemplary monoclonal antibody UC1MT, which is described in US 2003/0007973 and is commercially available from Abcam Inc, Cambridge, Mass. Clone UC1MT has also been described by Lynes et al. (Toxicology 1993 (85): 161-177).

In one embodiment, the antibody used in the methods described herein is a humanized antibody. Humanized antibodies refer to forms of non-human (e.g. murine) antibodies that are specific chimeric immunoglobulins, immunoglobulin chains, or antigen-binding fragments thereof that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, FAT framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs "derived from" one or more CDRs from the original antibody. Humanized antibodies may also involve affinity maturation.

As used herein, "treat" or "treating" means accomplishing one or more of the following in an individual that has one or more of the recited disorders: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and/or (e) limiting or preventing recurrence of symptoms in patients that were previously symptomatic for the disorder(s). Any amount of such "treating" is of great benefit to a subject one of the recited disorders.

As used herein, "limit" or "limiting development of" means accomplishing one or more of the following in an individual that is at risk one or more of the recited disorders: (a) slowing progression to the disorder and/or (b) limiting or preventing development of symptoms characteristic of progression to the disorder. Any amount of such "limiting development" is of great benefit to a subject at risk of one of the recited disorders.

Such treating or limiting development of may comprise use of the extracellular MT inhibitor as the sole therapeutic, or may comprise its use to complement or augment other therapeutic interventions, as deemed appropriate by attending medical personnel.

In one embodiment, the subject has diabetes or is at risk of developing diabetes, and the method serves to treat or limit development of diabetes.

In one such embodiment, the subject is at risk of type 1 diabetes, and the method serves to limit development of type I diabetes in the subject. As shown in the examples that follow, human MT1 inhibitors prevented development of type 1 diabetes in the NOD mouse model. Thus, the methods of this embodiment can be used to limit development of type 1 diabetes (T1D) in subjects at risk of T1D. Limiting development of T1D may include, but is not limited to, slowing progression to T1D and/or slowing development of symptoms characteristic of T1D. In this embodiment, the subject at risk for T1D has one or more risk factor for T1D from which attending medical personnel deems the treatment to be appropriate. Such risk T1D risk factors include, but are not limited to: a parent or sibling with type 1 diabetes, a pancreatic tumor, pancreatitis, pancreatic islet cell autoantibodies, insulin autoantibodies, glutamic acid decarboxylase autoantibodies (GADA), insulinoma-associated (IA-2) autoantibodies, zinc transporter autoantibodies (ZnT8), and/or variants of the IDDM1 gene selected from the group consisting of DRB1 0401, DRB1 0402, DRB1 0405, DQA 0301, DQB1 0302 and DQB1 0201. Alternatively, or in combination, the subject may exhibit one or more symptom of T1D (but not yet be diagnosed with T1D); such symptoms may include, but are not limited to polyuria (increased urination), polydipsia (increased thirst), dry mouth, polyphagia (increased hunger), fatigue, and weight loss. As will be understood by those of skill in the art, any limit on the development of T1D or its symptoms provides a great benefit a subject at risk The Insulin-dependent (type I) diabetes mellitus 1 (IDDM1) gene is located in the MHC Class II region on chromosome 6. Certain variants of this gene increase the risk for decreased histocompatibility characteristic of type 1 diabetes. Such variants include DRB1 0401, DRB1 0402, DRB1 0405, DQA 0301, DQB1 0302 and DQB1 0201. Similarly, the appearance of diabetes-related autoantibodies such as pancreatic islet cell autoantibodies, insulin autoantibodies, glutamic acid decarboxylase autoantibodies (GADA), insulinoma-associated (IA-2) autoantibodies, zinc transporter autoantibodies (ZnT8) often predate the hyperglycemia diabetes type 1 before any hyperglycemia arises. The risk of T1D increases with the number of antibody types, and the time interval from emergence of autoantibodies to clinically diagnosable T1D can be a few months in infants and young children, but in some people it may take years. Such autoantibodies can be detected by, for example, immunofluorescence or binding assays.

In another embodiment, the subject has type 1 diabetes, and the method serves to treat type I diabetes in the subject. In this embodiment, the subject has already been diagnosed with T1D, and the methods can be used to treat T1D. T1D involves autoimmune destruction of beta cells in the pancreas, little to no insulin production, and hyperglycemia. Treating T1D thus involves administration of insulin to the subject. Subjects with T1D may have symptoms or complications including but not limited to hypoglycemia, polyuria, polyphagia, polydipsia, weight loss, blurred vision, fatigue, decreased wound healing capability, urinary tract infections, sexual dysfunction, dry mouth, diabetic ketoacidosis, cardiovascular disease, diabetic nephropathy, diabetic neuropathy, diabetic retinopathy, stroke, kidney failure, and foot ulcers. In some cases, a subject having T1D may require a pancreatic or pancreatic islet transplant. Thus, in various embodiments, the treating may comprise one or more of: reducing frequency of need for insulin injection; slowing development or progression of type 1 diabetes complications in the subject including but not limited to destruction of pancreatic beta cells, hyperglycemia, hypoglycemia, polyuria, polyphagia, polydipsia, weight loss, blurred vision, fatigue, decreased wound healing capability, urinary tract infections, sexual dysfunction, dry mouth, diabetic ketoacidosis, cardiovascular disease, diabetic nephropathy, diabetic neuropathy, diabetic retinopathy, stroke, kidney failure, and foot ulcers; and delaying need for a pancreatic or pancreatic islet cell transplant. In one embodiment, the treating may comprise a reduction of 10%, 15%, 20% or greater in blood glucose levels (mg/dL), such as, for example, within 20-120 minutes after administration of the inhibitor.

In another embodiment, the subject is at risk of type 2 diabetes, and the method serves to limit development of type 2 diabetes (T2D) in the subject. T2D is a metabolic disorder characterized by hyperglycemia, insulin resistance, and relative lack of insulin. Symptoms and/or complications include, but are not limited to, hypoglycemia, insulin resistance, diabetic nephropathy, diabetic neuropathy, diabetic retinopathy, proteinuria, impaired glomerular clearance, diabetic circulatory disorders, kidney failure, cardiovascular disease, polyuria, polydipsia, weight loss, and stroke. In one embodiment, the limiting development of type 2 diabetes may comprise a reduction of 10%, 15%, 20% or greater in blood glucose levels (mg/dL), such as, for example, within 20-120 minutes after administration of the inhibitor.

Risk factors for T2D include, but are not limited to, obesity, smoking, a sedentary lifestyle, a parent or sibling with type 2 diabetes, pre-diabetes, a parent or sibling with pre-diabetes, poor eating habits (ex: too much fat, not enough fiber, too many simple carbohydrates, etc.), age 50 or older, high blood pressure, high cholesterol, testosterone deficiency, metallothionein 1 A (MT1A) rs8052394 locus (G alteration) single nucleotide polymorphism, and a history of gestational diabetes. Thus, in various embodiments the subject has one or more of these risk factors, and the method serves to slow progression to T2D and/or (b) limit or prevent development of symptoms characteristic of T2D.

As disclosed in the examples that follow, the methods of significantly improve glucose tolerance in a mouse model of T2D. Thus, in another embodiment, the subject has T2D, and the method serves to treat T2D in the subject. In this embodiment, the treating may comprise limiting one or more of type 2 diabetic complications, including but not limited to hyperglycemia, hypoglycemia, insulin resistance, diabetic nephropathy, diabetic neuropathy, diabetic retinopathy, proteinuria, impaired glomerular clearance, diabetic circulatory disorders, kidney failure, cardiovascular disease, polyuria, polydipsia, weight loss, stroke, and reducing frequency of need for insulin or other therapy. Any amount of limiting of these symptoms/complications is of great benefit to a subject with T2D. In one embodiment, the treating may comprise a reduction of 10%, 15%, 20% or greater in blood glucose levels (mg/dL), such as, for example, within 20-120 minutes after administration of the inhibitor.

In another embodiment, the subject has pre-diabetes, and the method serves to treat pre-diabetes in the subject. In this embodiment, the subject is one who has pre-diabetes. As used herein, "pre-diabetes" is the state in which some but not all of the diagnostic criteria for diabetes are met. Thus, the prediabetic subject may: (a) have impaired fasting glucose tolerance, which is a condition whereby the response of beta cells to an oral glucose challenge (OGT) is deficient or (b) may have consistently elevated fasting glucose (IFG), which is a condition in which the fasting blood glucose is elevated above what is considered normal levels but is not high enough to be classified as diabetes mellitus. The pre-diabetic state may be associated with insulin resistance and increased risk of cardiovascular pathology. Individuals with a pre-diabetic state are at a relatively high risk of developing T2D. The methods of the disclosure can be used to treat a subject with pre-diabetes by, for example, limiting or slowing progression of one or more complications of pre-diabetes, including but not limited to T2D, hyperglycemia, insulin resistance, and/or cardiovascular disease. In one embodiment, the treating may comprise a reduction of 10%, 15%, 20% or greater in blood glucose levels (mg/dL), such as, for example, within 20-120 minutes after administration of the inhibitor.

In another embodiment, the subject has impaired glucose intolerance, and the method serves to treat impaired glucose tolerance in the subject. As used herein, impaired glucose tolerance is defined as two-hour glucose levels of 140 to 199 mg per dL (7.8 to 11.0 mmol/1) on the 75-g oral glucose tolerance test. A patient is said to be under the condition of IGT when he/she has an intermediately raised glucose level after 2 hours, but less than the level that would qualify for type 2 diabetes mellitus. The fasting glucose may be either normal or mildly elevated. Impaired glucose tolerance is a pre-diabetic state of hyperglycemia that is associated with insulin resistance and increased risk of cardiovascular pathology. IGT may precede type 2 diabetes mellitus by many years. In this embodiment, the treating may comprise limiting or slowing progression of one or more complications of impaired glucose tolerance, including but not limited to type 2 diabetes, hyperglycemia, insulin resistance, and/or cardiovascular disease. In one embodiment, the treating may comprise a reduction of 10%, 15%, 20% or greater in blood glucose levels (mg/dL), such as, for example, within 20-120 minutes after administration of the inhibitor.

In another embodiment, the subject has hepatitis, and the method serves to treat hepatitis in the subject. As disclosed in the examples below, MT inhibitors are effective in limiting tissue inflammation, and decreased pro-inflammatory cytokines MCP-1 and TNF-a while increasing the anti-inflammatory IL-10 signal in liver tissue. Hepatitis is an inflammation of the liver tissue. Symptoms include, but are not limited to yellow discoloration of the skin and whites of the eyes, poor appetite, vomiting, tiredness, abdominal pain, diarrhea, acute liver failure, scarring of the liver, liver failure, or liver cancer. The most common causes of hepatitis are viral infections (types A, B, C, D, and E), heavy alcohol use, certain medications, toxins, other infections, autoimmune diseases, and non-alcoholic steatohepatitis (NASH). Thus, in various embodiments the treating may comprise limiting or slowing progression of one or more complications of hepatitis, including but not limited to yellow discoloration of the skin and/or whites of the eyes, poor appetite, vomiting, fatigue, abdominal pain, diarrhea, acute liver failure, scarring of the liver, liver failure, and liver cancer.

In a further embodiment, the subject has an inflammatory liver disease, and the method serves to treat the inflammatory liver disease in the subject. As used herein, "Inflammatory liver disease" is a condition associated with intracytoplasmic accumulation of large vacuoles of triglyceride fat in liver cells via steatosis (i.e., abnormal retention of lipids within a cell). The liver plays a large role in systemic metabolism and energy imbalance is particularly associated with defects in liver lipid metabolism. Specifically, obesity and insulin resistance are often associated by increased lipid deposition in the liver characteristic of nonalcoholic fatty liver disease (NAFLD). Although lipid metabolism is highly dynamic, chronic lipid overload causes tissue damage in the liver resulting in recruitment of liver-resident and non-resident immune cells which can cause fibrosis characteristic of nonalcoholic steatohepatitis (NASH). Liver fibrosis can lead to cirrhosis, cancer and significantly increases the risk of cardiovascular disease. This raises the potential for blocking recruitment of immune cells to the liver to ameliorate the risks of non-alcoholic fatty liver disease (NAFLD). As shown in the examples that follow, MT inhibitor treatment was responsible for an increase in the wet tissue weight of epididimal white adipose tissue, and decreased total triglyceride levels, as well as decreased pro-inflammatory cytokines MCP-1 and TNF-a while increasing the anti-inflammatory IL-10 signal. The inflammatory liver disease may be steatosis (non-alcoholic fatty liver (NAFL)). In another embodiment, fatty liver disease may non-alcoholic fatty liver disease (NAFLD), including but not limited to non-alcoholic steatohepatitis (NASH), the most extreme form of NAFLD. NAFLD is one of the types of inflammatory liver disease which occurs when fat is deposited (steatosis) in the liver due to causes other than excessive alcohol use. Symptoms of NASH and NAFLD may include, but are not limited to, fatigue, malaise, dull right-upper-quadrant abdominal discomfort, mild jaundice, and abnormal liver function tests during routine blood tests; complications of NASH and NAFLD may include, but are not limited to hepatic fibrosis, hepatic cancer, and/or cirrhosis of the liver. Thus, in one embodiment, the inflammatory liver disease is selected from the group consisting of nonalcoholic steatohepatitis (NASH) and/or non-alcoholic fatty liver disease (NAFLD). In a further embodiment, the treating comprises limiting or slowing progression of one or more complications of inflammatory liver disease including but not limited to fatigue, malaise, hepatic fibrosis, hepatic cancer, and/or cirrhosis of the liver.

In one embodiment, the MT inhibitor, including but not limited to an anti-MT antibody, may be linked to a pancreatic cell targeting moiety, to specifically target pancreatic cells producing MT, such as pancreatic beta cells. This embodiment will be particularly useful for treating or limiting development of T1D, T2D, pre-diabetes, and/or impaired glucose tolerance. In one embodiment, the pancreatic β cell specific targeting moiety comprises one or more peptides or other moieties that preferentially bind pancreatic β cells, including but not limited to glucagon-like peptide-1 (GLP-1), glucagon-like peptide-2 (GLP-2), peptide YY (PYY), neuropeptide Y (NPY), pancreatic peptide (PPY), and exendin-4.

```
Glucagon-like peptide 1; GLP1(aa92-128)
                                         (SEQ ID NO: 9)
HDEFERHAEGTFTSDVSSYLEGQAAKEFIAWLVKGRG Glucagon-like peptide 2; GLP2(aa146-178)
                                         (SEQ ID NO: 10)
HADGSFSDEMNTILDNLAARDFINWLIQTKITD pancreatic peptide (PPY)
                                         (SEQ ID NO: 11)
MAAARLCLSLLLLSTCVALLLQPLLGAQGAPLEPVYPGDNATPEQMAQYA

ADLRRYINMLTRPRYGKRHKEDTLAFSEWGSPHAAVPRELSPLDL neuropeptide Y (NPY)
                                         (SEQ ID NO: 12)
MLGNKRLGLSGLTLALSLLVCLGALAEAYPSKPDNPGEDAPAEDMARYYS

ALRHYINLITRQRYGKRSSPETLISDLLMRESTENVPRTRLEDPAMW peptide YY (PYY)
                                         (SEQ ID NO: 13)
MVFVRRPWPALTTVLLALLVCLGALVDAYPIKPEAPGEDASPEELNRYYA

SLRHYLNLVTRQRYGKRDGPDTLLSKTFFPDGEDRPVRSRSEGPDLW exendin-4
                                         (SEQ ID NO: 14)
MKIILWLCVFGLFLATLFPISWQMPVESGLSSEDSASSESFASKIKRHGE

GTFTSDLSKQMEEEAVRLFIEWLKNGGPSSGAPPPSG
```

Attaching the pancreatic cell targeting moiety to the MT inhibitor, including but not limited to the MT antibody or fragment thereof, or the aptamer, may be accomplished by any chemical reaction that will bind the two molecules so long as the pancreatic cell targeting moiety and the MT antibody or fragment thereof, or the aptamer, retain their respective activities. In one embodiment where the extracellular MT inhibitor comprises an antibody or fragment thereof, the composition comprises a recombinant fusion protein. In other embodiments, a linkage between the pancreatic cell targeting moiety and the MT antibody or fragment thereof can include many chemical mechanisms, for instance covalent binding, affinity binding, intercalation, coordinate binding and complexation. Covalent binding can be achieved either by direct condensation of existing side chains or by the incorporation of external bridging molecules. Many bivalent or polyvalent linking agents are useful in coupling protein molecules, such as the antibodies, to other molecules. For example, representative, non-limiting examples of coupling agents can be organic compounds such as thioesters, carbodiimides, succinimide esters, diso-cyanates, glutaraldehydes, diazobenzenes and hexamethylene diamines.

In all embodiments, the subject may be any subject that can benefit from the methods of treatment disclosed herein, including mammals, humans, cattle, dogs, cats, horses, chickens, and so on. In one embodiment, the subject is human.

The compositions for administration are typically formulated as a pharmaceutical composition to include a pharmaceutically acceptable carrier. Suitable acids which are capable of forming pharmaceutically acceptable salts include inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid and the like. Suitable bases capable of forming such salts include inorganic bases such as sodium hydroxide, ammonium hydroxide, potassium hydroxide and the like; and organic bases such as mono-, di- and tri-alkyl and aryl amines (e.g., triethylamine, diisopropyl amine, methyl amine, dimethyl amine and the like) and optionally substituted ethanolamines (e.g., ethanolamine, diethanolamine and the like).

The pharmaceutical composition may comprise in addition to the composition and carrier (a) a lyoprotectant; (b) a surfactant; (c) a bulking agent; (d) a tonicity adjusting agent; (e) a stabilizer; (f) a preservative and/or (g) a buffer. In some embodiments, the buffer in the pharmaceutical composition is a Tris buffer, a histidine buffer, a phosphate buffer, a citrate buffer or an acetate buffer. The pharmaceutical composition may also include a lyoprotectant, e.g. sucrose, sorbitol or trehalose. In certain embodiments, the pharmaceutical composition includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the pharmaceutical composition includes a bulking agent, like glycine. In yet other embodiments, the pharmaceutical composition includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The pharmaceutical composition may also include a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the pharmaceutical composition additionally includes a stabilizer, e.g., a molecule which, when combined with a protein-based composition substantially prevents or reduces chemical and/or physical instability of the protein in lyophilized or liquid form. Exemplary stabilizers include sucrose, sorbitol, glycine, inositol, sodium chloride, methionine, arginine, and arginine hydrochloride.

The compositions can be administered via any suitable route, including orally, parentally, by inhalation spray, rectally, or topically in dosage unit formulations containing conventional pharmaceutically acceptable carriers, adjuvants, and vehicles. The term parenteral as used herein includes, subcutaneous, intravenous, intra-arterial, intramuscular, intrasternal, intratendinous, intraspinal, intracranial, intrathoracic, infusion techniques or intraperitoneally. Dosage regimens can be adjusted to provide the optimum desired response (e.g., a therapeutic or prophylactic response). A suitable dosage range may, for instance, be 0.1 ug/kg-100 mg/kg body weight; alternatively, it may be 0.5 ug/kg to 50 mg/kg; 1 ug/kg to 25 mg/kg, or 5 ug/kg to 10 mg/kg body weight. The compositions can be delivered in a single bolus, or may be administered more than once (e.g., 2, 3, 4, 5, or more times) as determined by attending medical personnel. The compositions may be the sole therapeutic administered, or may be administered together with one or more other therapeutic (either separately or as a combination) as deemed appropriate by attending medical personnel. In one non-limiting embodiment, the subject has or is at risk of T1D and the inhibitor may be used together with one or more of insulin, metformin, or pramlintide. In another embodiment, the subject has or is at risk of T2D, prediabetes, and/or imparired glucose tolerance, and the inhibitor may be used together with one or more of metformin, sulfonylureas (including but not limited to glyburide, glipizide, and glimepiride), meglitinides (including but not limited to repaglinide and nateglinide), thiazolidinediones (including but not limited to rosiglitazone and pioglitazone), DPP-4 inhibitors (including but not limited to sitagliptin, saxagliptin, and linagliptin), GLP-1 receptor agonists (including but not limited to exenatide, liraglutide, and semaglutide), SGLT2 inhibitors (including but not limited to canagliflozin, dapagliflozin, and empagliflozin), or insulin. In one non-limiting embodiment, the subject has or is at risk of hepatitis, and the inhibitor may be used in combination with one or more of entecavir, tenofovir, lamivudine, adefovir, telbivudine, simeprevir, sofosbuvir, interferon or ribavirin.

In another embodiment, compositors are provided comprising
(a) an inhibitor of extracellular human metallothionein (MT); and
(b) one or more of insulin, metformin, pramlintide, a sulfonylurea (including but not limited to glyburide, glipizide, and glimepiride), a meglitinide (including but not limited to repaglinide and nateglinide), a thiazolidinedione (including but not limited to rosiglitazone and pioglitazone), a DPP-4 inhibitor (including but not limited to sitagliptin, saxagliptin, and linagliptin), a GLP-1 receptor agonist (including but not limited to exenatide, liraglutide, and semaglutide), a SGLT2 inhibitor (including but not limited to canagliflozin, dapagliflozin, and empagliflozin), entecavir, tenofovir, lamivudine, adefovir, telbivudine, simeprevir, sofosbuvir, interferon or ribavirin. The compositions may be used, for example, in the methods of the disclosure. In one embodiment, the inhibitor comprises an anti-metallothionein antibody or a fragment thereof which specifically binds to human metallothionein (MT). All embodiments and combinations of embodiments of antibodies disclosed above are suitable for inclusion in the compositions of this aspect. In one embodiment, the anti-MT antibody or an antigen-binding fragment thereof comprises a monoclonal antibody or an antigen binding fragment thereof. In another embodiment the anti-MT antibody comprises a humanized anti-MT antibody, or an antigen binding fragment thereof.

In another aspect, the disclosure provides compositions, comprising:
(a) an inhibitor of extracellular human metallothionein (MT); and
(b) a pancreatic or hepatic cell targeting moiety linked to the inhibitor of extracellular human MT.

The compositions may be used, for example, in the methods of the disclosure. In one embodiment, the inhibitor comprises an anti-metallothionein antibody or a fragment thereof which specifically binds to human metallothionein (MT). All embodiments and combinations of embodiments of antibodies disclosed above are suitable for inclusion in the compositions of this aspect. In one embodiment, the anti-MT antibody or an antigen-binding fragment thereof comprises a monoclonal antibody or an antigen binding fragment thereof. In another embodiment the anti-MT antibody comprises a humanized anti-MT antibody, or an antigen binding fragment thereof.

In one embodiment, the cell targeting moiety is a hepatic cell targeting moiety. In exemplary such embodiments, wherein the hepatic cell targeting moiety includes but is not limited to circumsporozoite protein (CSP), CSP region I, CSP region I-plus, lactosaminated human serum albumin, glycosylated lipoprotein, and/or arabinogalactan. In one embodiment, the hepatic cell binding moeity is peptidic and selected from CSP, CSP region I, CSP region I plus, or hepatic cell binding fragments thereof. CSP targets *Plasmodium* sporozoite to the liver is attributed to the circumsporozoite protein (CSP), which is present on the surface of *Plasmodium* sporozoite (Rathore D, et al. *The Journal of Biological Chemistry*. 2005; 280(21):20524-20529) CSP is approximately 400 amino acids long organized into three domains: the N-terminal domain containing a conserved KLKQP motif named "region I", a highly repetitive central domain, and a C-terminal domain containing another conserved sequence named "region II" (Singh et al. Cell. 2007; 131(3):492-504). In addition to the conserved region I KLKQP (SEQ ID NO: 15) sequence, the N-terminal region also contains upstream from region I, two consensus heparin sulfate binding sequences. Peptides containing both the conserved region I amino acids and two consensus heparin binding sequences upstream from region I have been named "region I-plus" (Prudêncio et al., *Nature Reviews Microbiology*. 2006; 4(11):849-856).

In another embodiment, the cell targeting moiety is a pancreatic cell targeting moiety, including but not limited to glucagon-like peptide-1 (GLP-1), glucagon-like peptide-2 (GLP-2), peptide YY (PYY), neuropeptide Y (NPY), pancreatic peptide (PPY), and exendin-4; exemplary amino acid sequences for such peptides are described above.

Attaching the cell targeting moiety to the MT inhibitor, including but not limited to the MT antibody or fragment thereof, or the aptamer, may be accomplished by any chemical reaction that will bind the two molecules so long as the cell targeting moiety and the MT antibody or fragment thereof, or the aptamer, retain their respective activities. In one embodiment where the extracellular MT inhibitor comprises an antibody or fragment thereof and the cell targeting moiety is peptidic, the composition comprises a recombinant fusion protein. In other embodiments, a linkage between the cell targeting moiety and the MT antibody or fragment thereof can include many chemical mechanisms, for instance covalent binding, affinity binding, intercalation, coordinate binding and complexation. Covalent binding can be achieved either by direct condensation of existing side chains or by the incorporation of external bridging molecules. Many bivalent or polyvalent linking agents are useful in coupling protein molecules, such as the antibodies, to other molecules. For example, representative, non-limiting examples of coupling agents can be organic compounds such as thioesters, carbodiimides, succinimide esters, diisocyanates, glutaraldehydes, diazobenzenes and hexamethylene diamines.

In another aspect, the disclosure provides recombinant nucleic acids encoding recombinant fusion polypeptides of anti-MT antibodies, or fragments thereof fused to the peptidic targeting moieties, including those specifically disclosed herein. The recombinant nucleic acid sequence may comprise single stranded or double stranded RNA or DNA, and derivatives thereof. Such recombinant nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals.

In a further aspect are disclosed recombinant expression vectors comprising the recombinant nucleic acid of any embodiment or combination of embodiments of the disclosure operatively linked to a suitable control sequence. "Recombinant expression vector" includes vectors that operatively link a nucleic acid coding region or gene to any control sequences capable of effecting expression of the gene product. "Control sequences" operably linked to the nucleic acid sequences of the invention are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operatively linked" to the coding sequence. Other such control sequences include, but are not limited to, polyadenylation signals, termination signals, and ribosome binding sites. Such expression vectors can be of any type, including but not limited to plasmid and viral-based expression vectors. The expression vector may be replicable in the host organisms either as an episome or by integration into host chromosomal DNA. In non-limiting embodiments, the expression vector may comprise a plasmid or a viral vector.

In another aspect, the present disclosure provides recombinant host cells that comprise the recombinant expression vectors disclosed herein, wherein the host cells can be either prokaryotic or eukaryotic, such as mammalian cells. The cells can be transiently or stably transfected.

In another embodiment are disclosed uses of the compositions, the recombinant nucleic acids, the recombinant expression vectors, the recombinant host cells, or the pharmaceutical compositions of any embodiment or combination of embodiments disclosed herein, to treat or limit development of a disorder selected from the group consisting of diabetes, pre-diabetes, impaired glucose tolerance, hepatitis, and/or inflammatory liver disease. Such uses are as described above.

In a further embodiment are disclosed methods to treat or limit development of a disorder selected from the group consisting of diabetes, pre-diabetes, impaired glucose tolerance, hepatitis, and/or inflammatory liver disease by administering to a subject in need thereof an amount effective to treat the disorder of the compositions, the recombinant nucleic acids, the recombinant expression vectors, the recombinant host cells, or the pharmaceutical compositions of any embodiment or combination of embodiments disclosed herein. Such methods are as described above.

EXAMPLES

Treating Type 2 Diabetes with UC1MT

Figure 2:
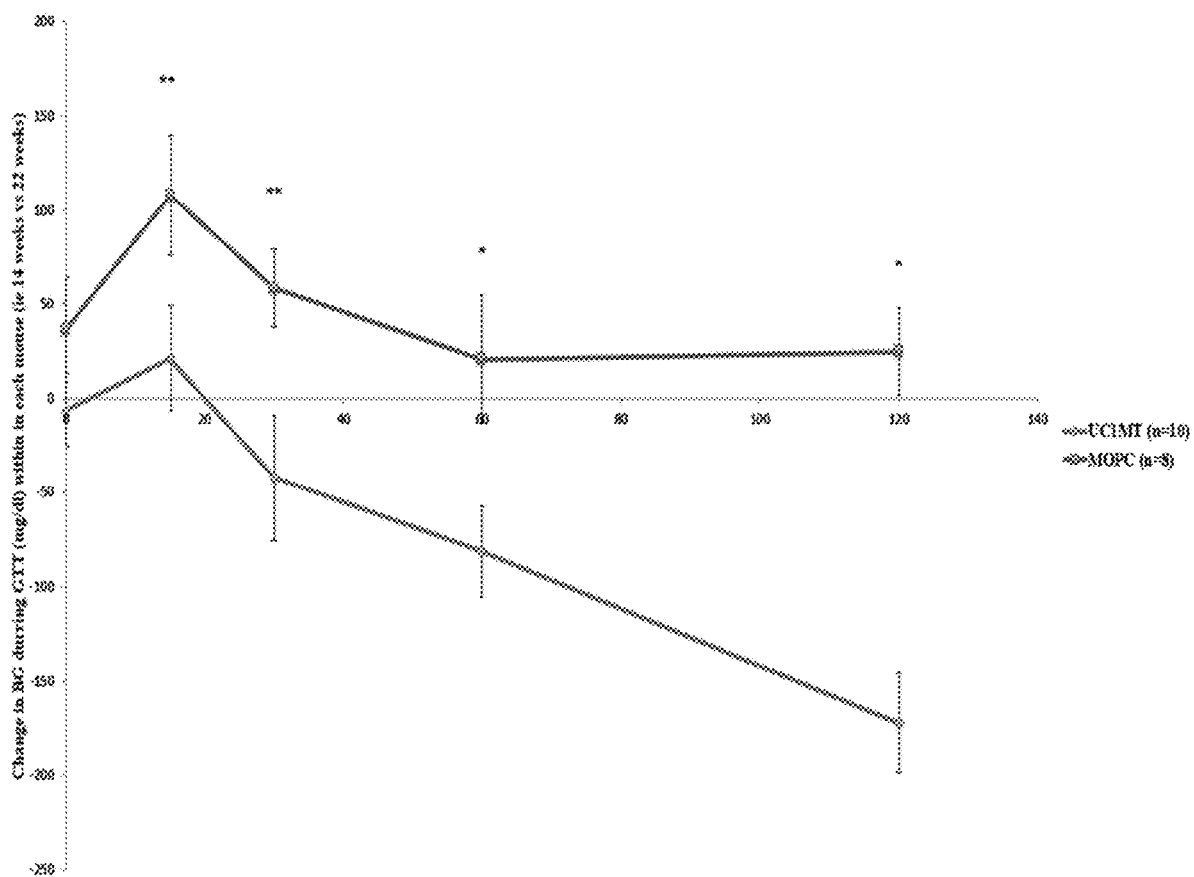
FIG. 2. Graph showing the change in glucose tolerance test results normalized to the initial measure from each animal in the group depicted in FIG. 1.

To model the insulin resistance characteristic of Type II diabetes, we fed mice a high fat diet (HFD). Five week old C57BL/6J mice were fed a standard 60% high fat diet for 14 weeks before treatment was initiated. The mice were injected twice weekly IP with 100 µl of 1 mg/ml of an anti-MT antibody (UC1MT; obtained from Abcam Inc, Cambridge, Mass) for eight weeks and then the mice were sacrificed at 27 weeks of age (for a total of 22 weeks of HFD). There was no difference in either body weight or food intake between the two treatment groups. FIG. 1 shows the results of glucose tolerance testing of mice injected with glucose intraperitoneally at the end of the course of treatment with IgG1 isotype control (MOPC21) or UC1MT. FIG. 2 shows the change in glucose tolerance test results normalized to the initial measure from each animal in the group. Control animals developed fatty liver and glucose intolerance, however mice treated with UC1MT showed improved glucose tolerance compared to controls. These data demonstrate that anti-MT antibodies can be used to treat impaired glucose tolerance. Since glucose tolerance can be modulated by inflammatory status, these results also suggest that UC1MT improves the inflammatory profile of the mice, and thus improves the ability of the HFD-fed mice to manage a large glucose challenge.

Effects on NASH (Non-Alcoholic Steatohepatitis) Liver Inflammatory Profile in HFD Fed Mice Treated with UC1MT or MOPC21

The liver plays a large role in systemic metabolism and energy imbalance is particularly associated with defects in liver lipid metabolism. Specifically, obesity and insulin resistance are often associated by increased lipid deposition in the liver characteristic of nonalcoholic fatty liver disease (NAFLD) (Katsiki N et al, Metabolism 2016 PMID: 27237577). Although lipid metabolism is highly dynamic (Sakaguchi M et al, Cell Metab 2017 PMID: 28065828), chronic lipid overload causes tissue damage in the liver resulting in recruitment of liver-resident and non-resident immune cells which can cause fibrosis characteristic of nonalcoholic steatohepatitis (NASH) (Narayanan S et al, Immune Netw 2016 PMID: 27340383). Liver fibrosis can lead to cirrhosis, cancer and significantly increases the risk of cardiovascular disease. This raises the potential for blocking recruitment of immune cells to the liver to ameliorate the risks of non-alcoholic fatty liver disease (NAFLD).

Figure 3:
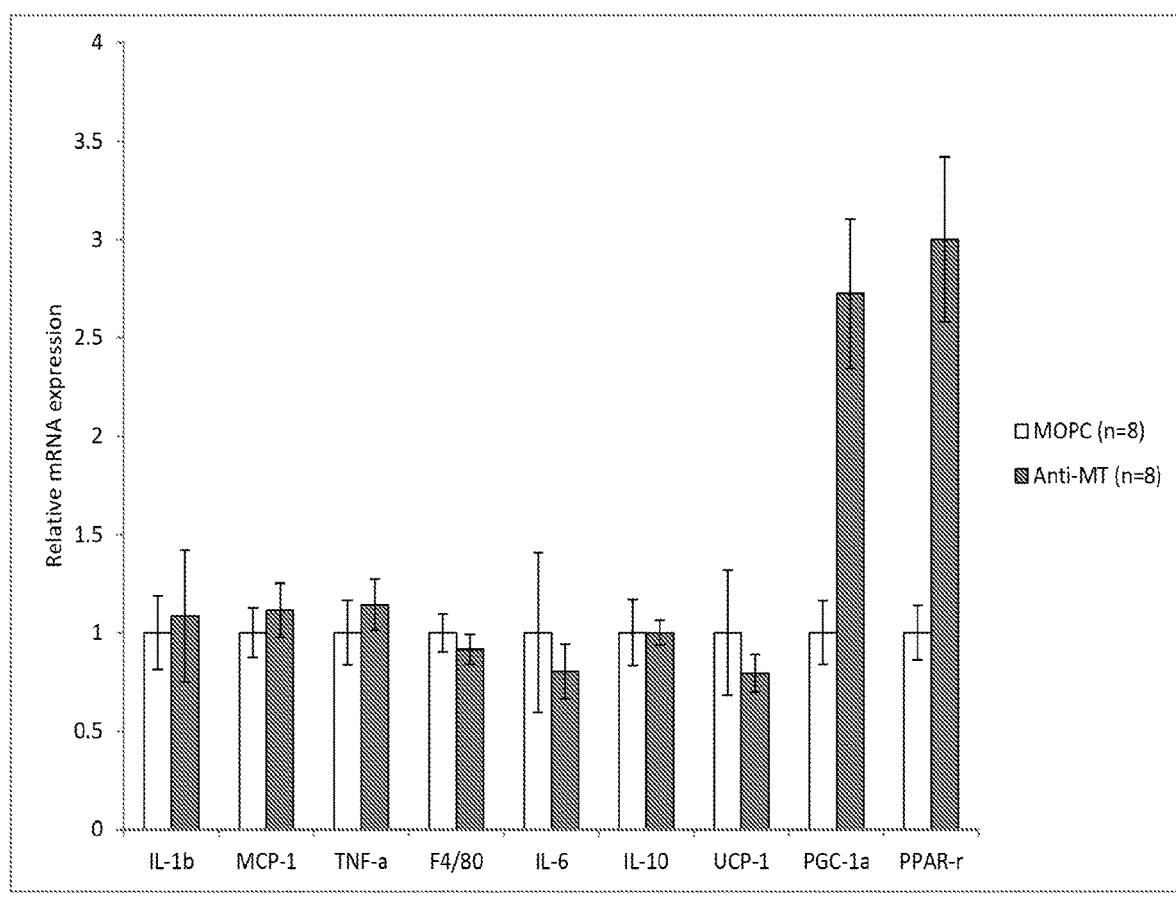
FIG. 3. Graph showing effects of MOPC21 or UC1MT on RNA expression levels in the epididymal white adipose tissue via qPCR studies. UC1MT treatment had effects on some of the gene expression of white epididymal adipose tissue (notably Peroxisome proliferator-activated receptor gamma coactivator 1-alpha (PGC-1a), a transcriptional coactivator that regulates energy metabolism, and Peroxisome proliferator-activated receptor alpha (PPAR-r)).

The same animals described above in the Type 2 diabetes study were examined for liver phenotype by assessing mRNA expression via qPCR studies. UC1MT treatment had effects on some of the gene expression of white epididimal adipose tissue (notably Peroxisome proliferator-activated receptor gamma coactivator 1-alpha (PGC-1a), a transcriptional coactivator that regulates energy metabolism, and Peroxisome proliferator-activated receptor (PPAR gamma)) (FIG. 3).

Figure 4:
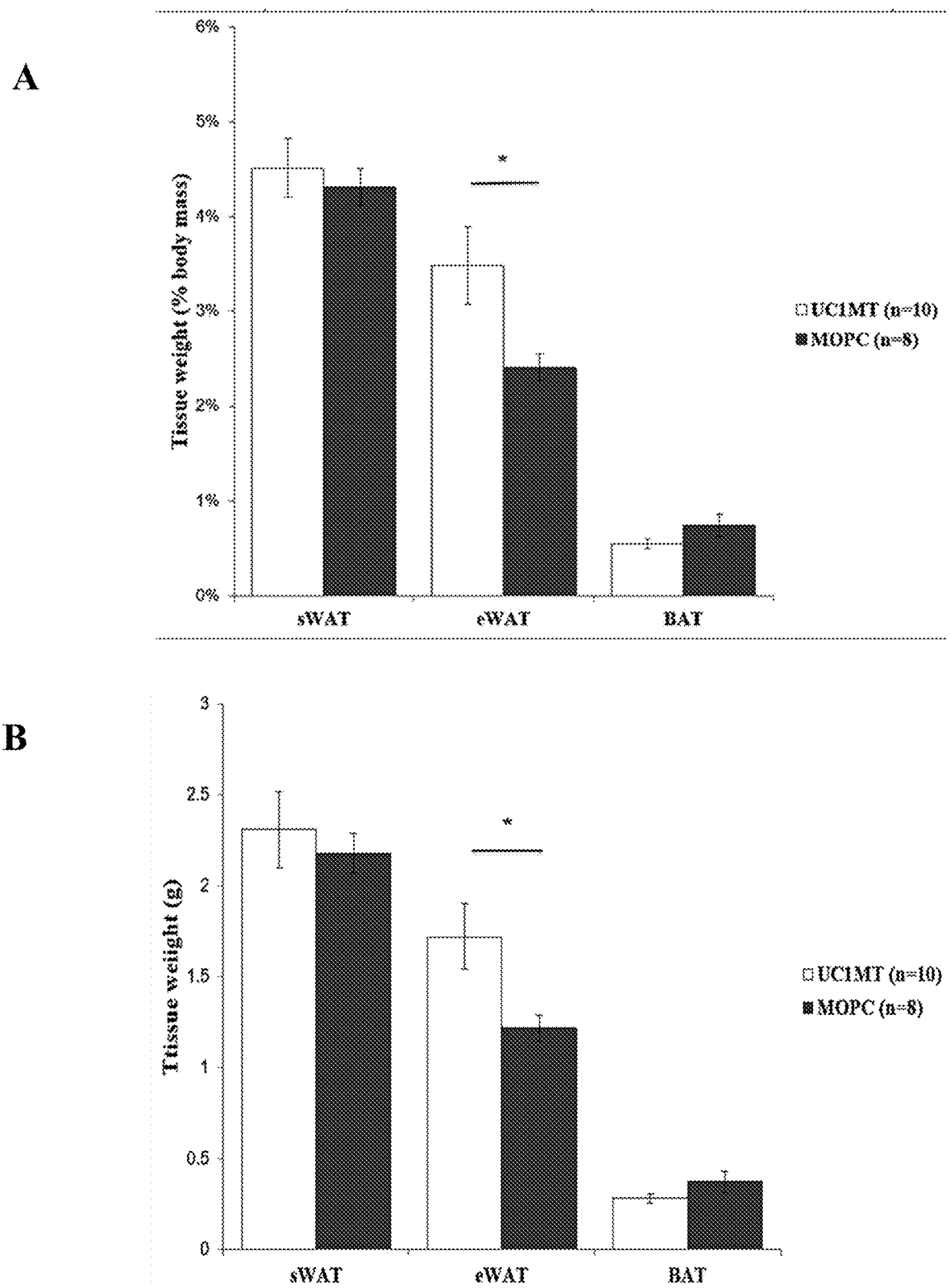
FIG. 4. Graphs showing the effect of antibody treatment on adipose tissue weights: (A) Tissue weight as percent of body mass; (B) Tissue weight in grams. Note changes in epididymal white adipose tissue (eWAT). (BAT=Brown adipose Tissue; sWAT=subcutaneous white adipose tissue).
Figure 5:
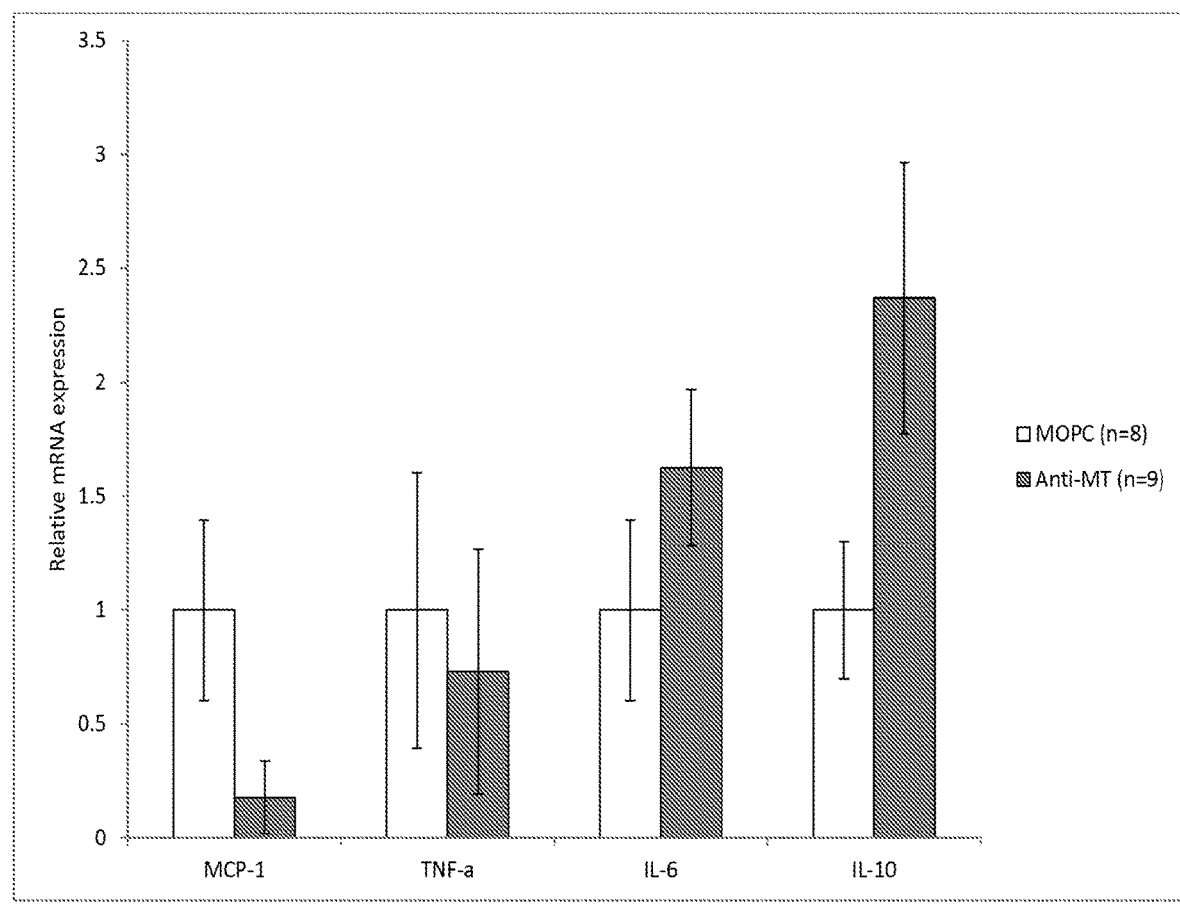
FIG. 5. Graph showing effects of MOPC21 or UC1MT on RNA expression levels in the liver via qPCR studies. There is substantial increase in the anti-inflammatory IL-10 gene expression that correlates with treatment with UC1MT in the high fat diet-treated mice than those HFD mice that were treated with the MOPC21 isotype matched control antibody.
Figure 6:
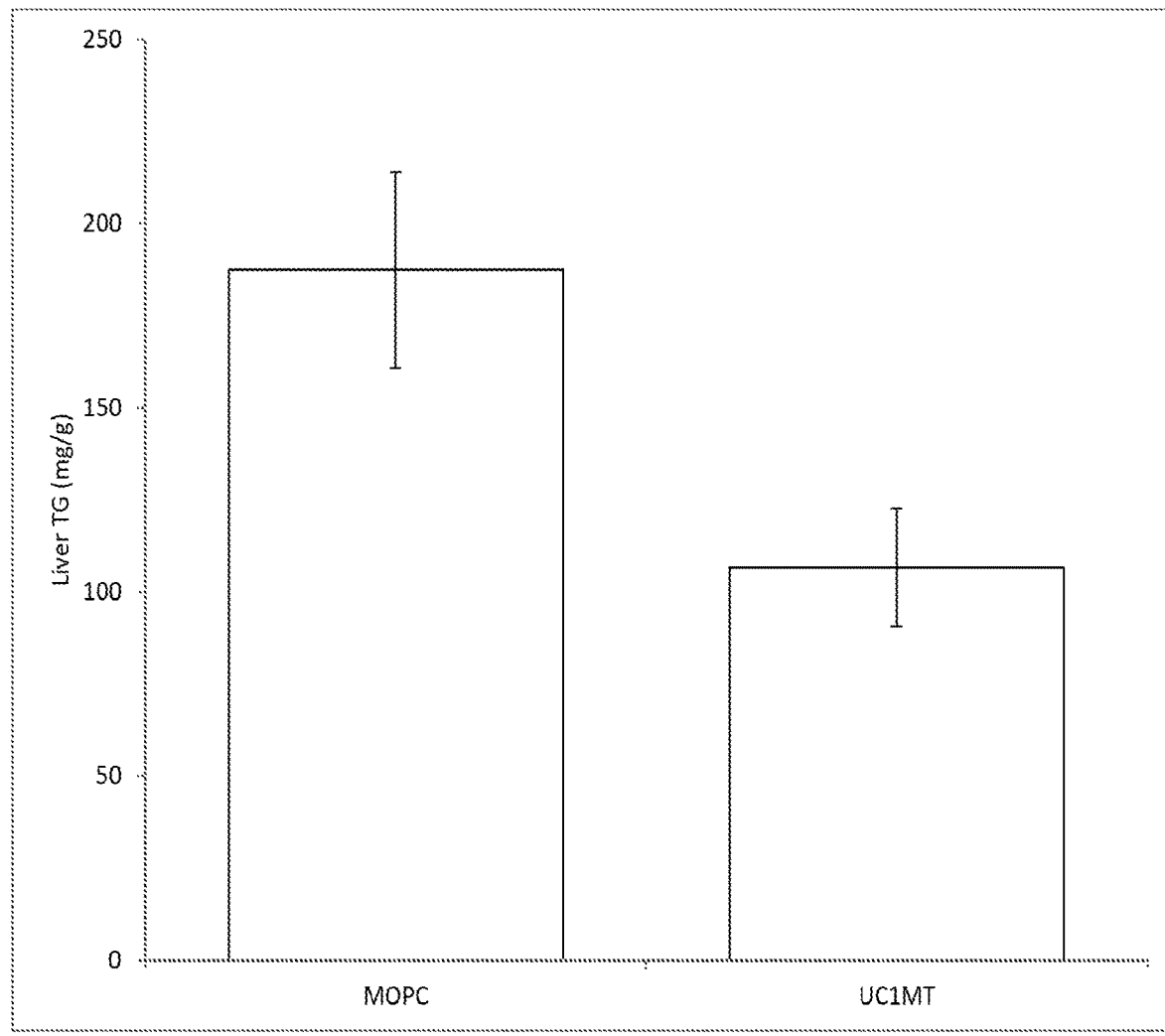
FIG. 6. Graph showing effects of MOPC21 or UC1MT on liver triglycerides using Thermo Fisher Trigylcerides kit (colorometric assay). Shown are mean and standard error N=8 MOPC, 10 UC1MT for male mice fed 16 weeks HFD. * p=0.0453 by 2 tailed Student's t test.

At sacrifice of the animals, liver, pancreas, squamous white adipose tissue, eWAT, intrascapular brown adipose tissue, and serum were collected. Half of each sample was used for RNA, half for histology (all tissues were fixed in formalin except pancreas which was fixed in Z-FIX™ (Fisher Scientific). The data show that the anti-MT antibody was responsible for:
- an increase in the wet tissue weight of epididimal white adipose tissue (FIG. 4A-B);
- decreased total triglyceride levels in the liver (FIG. 6);
- decreased expression of some pro-inflammatory cytokines (MCP-1 and TNF-a) (FIG. 5); and
- increased expression of the anti-inflammatory IL-10 signal (FIG. 5)

Anti-metallothionein antibody did not alter body weight or weight gain in high fat diet-treated mice, nor did it significantly alter liver histology.

Concordant with the improved glucose tolerance shown above, mice treated with anti-MT antibodies had decreased liver triglyceride levels. These data suggest that MT inhibitors can improve systemic glucose metabolism, which can decrease the burden of nutrient excess on the liver and limit development of hepatosteatosis.

Type 1 Diabetes Studies

The NOD/ShiLtJ mouse strain (commonly called NOD) is a polygenic model for autoimmune type 1 diabetes. Diabetes in NOD mice is characterized by hyperglycemia and insulitis, a leukocytic infiltration of the pancreatic islets. Marked decreases in pancreatic insulin content occur in females at about 12 weeks of age and several weeks later in males. 80% of females and 45% of males become diabetic by 30 weeks; median female incidence is 17 weeks. Immune phenotypes in the NOD background consist of defects in antigen presentation, T lymphocyte repertoire, NK cell function, macrophage cytokine production, wound healing, and C5 complement. These defects make the NOD background a common choice for immunodeficient mouse strains.

Figure 7:
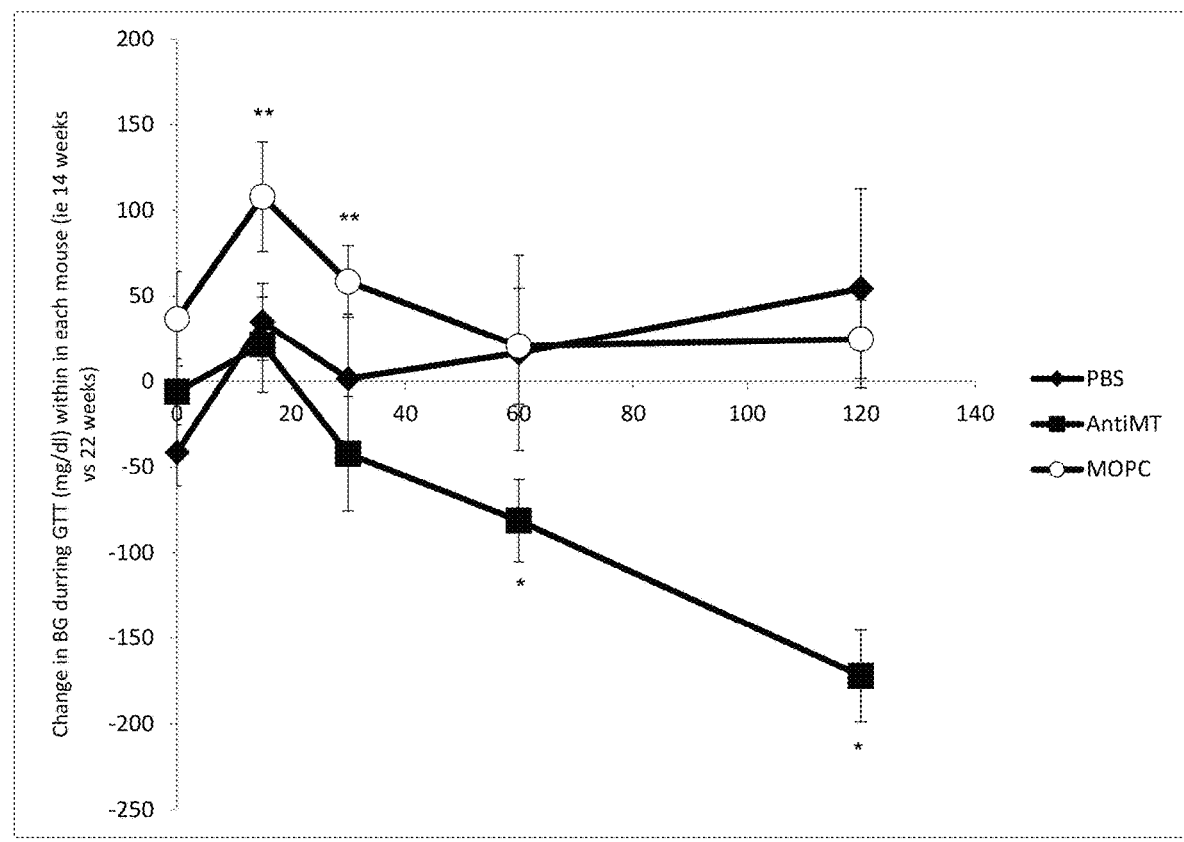
FIG. 7. Graph showing the effects of daily intraperitoneal injection of MOPC21 or UC1MT (100 ul per mouse for two weeks) on blood glucose levels in NOD mice over a 30 week time-course. UC1MT treatment prevented the T1D development in NOD mice.
Figure 8:
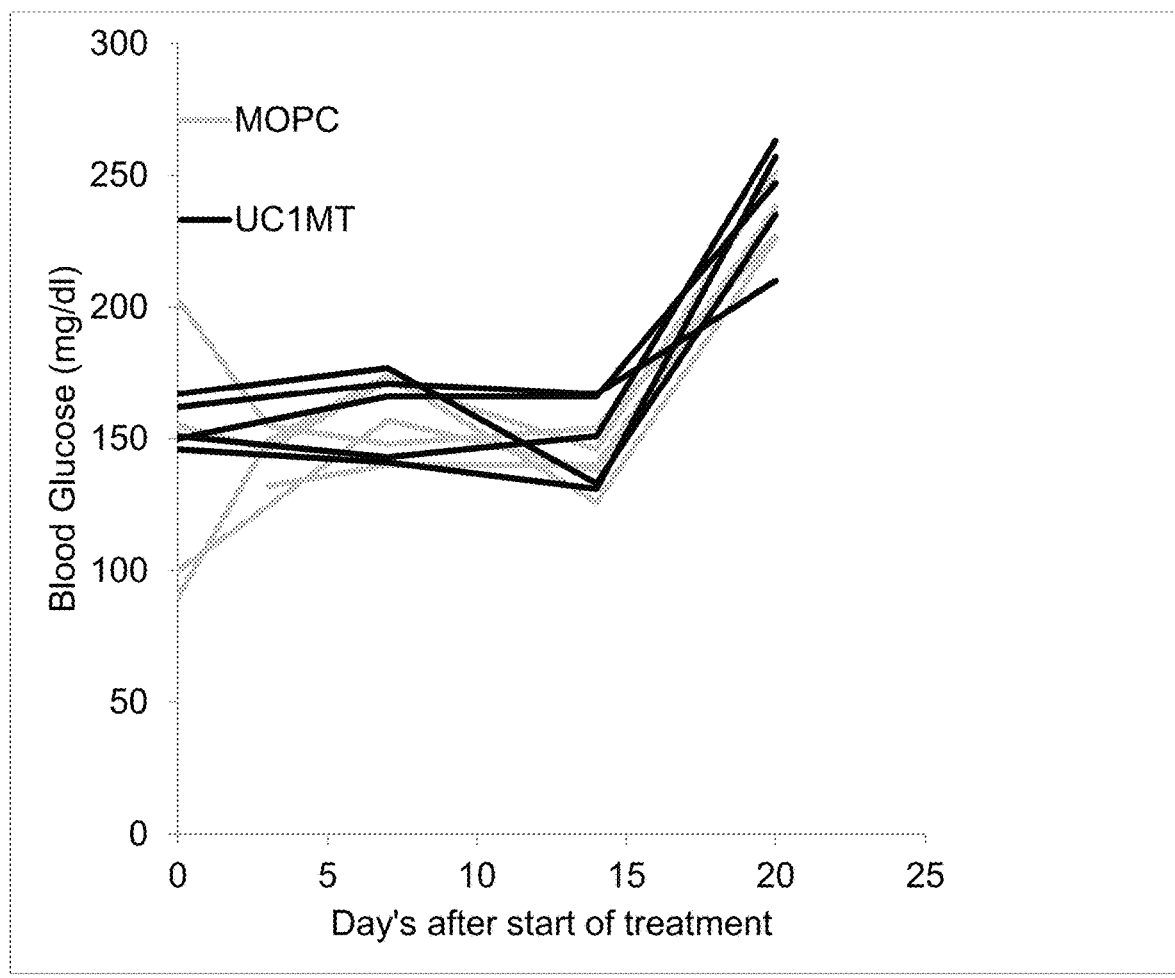
FIG. 8. Graphs showing effects of intraperitoneal injection of UC1MT or MOPC21, 100 ul per mouse (twice a week) on blood glucose level in mice over a 3 week (A) and 6 week (B) time course. UC1MT treatment prevented the T1D development in NOD mice.
Figure 8B:
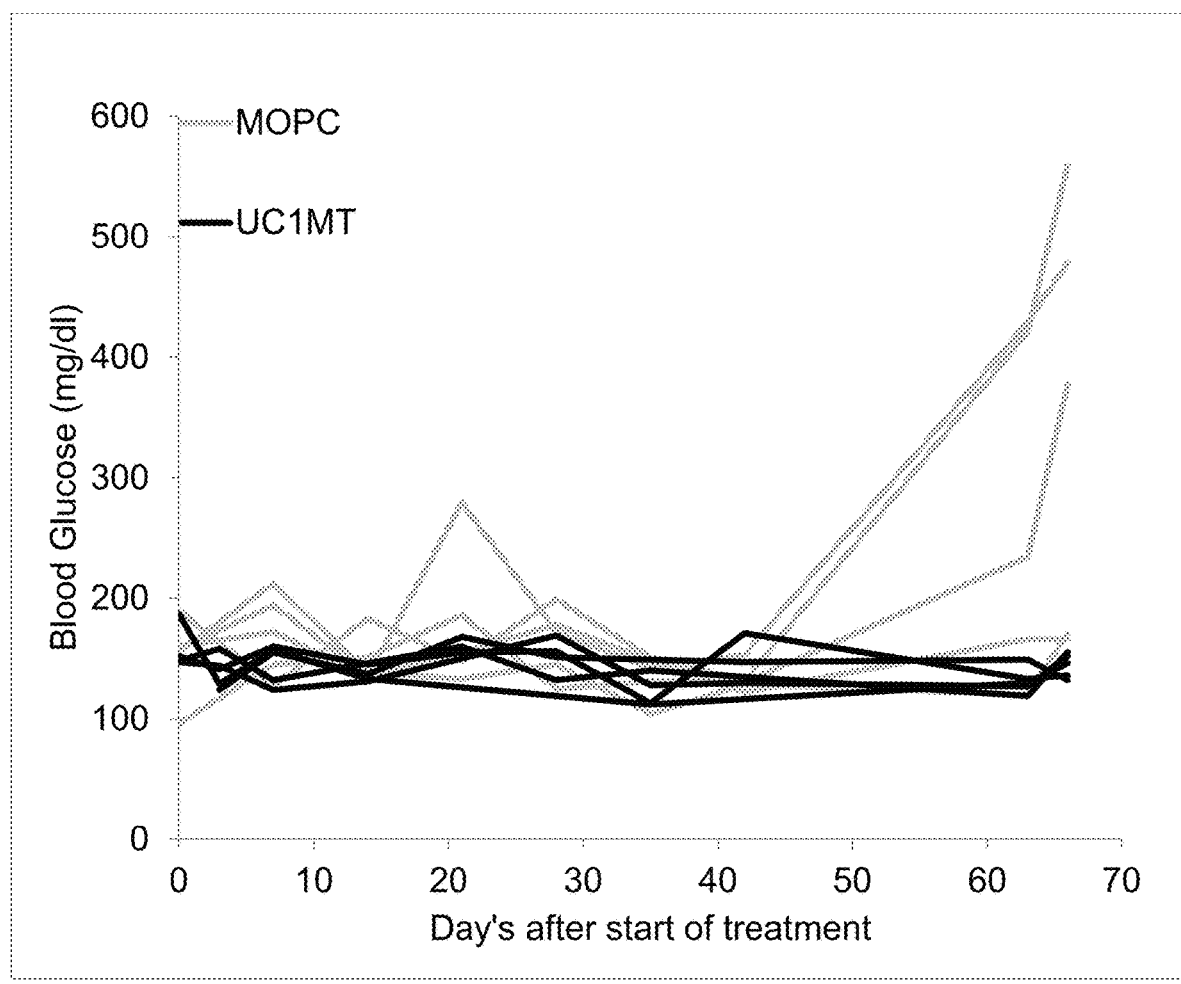
Figure 9:
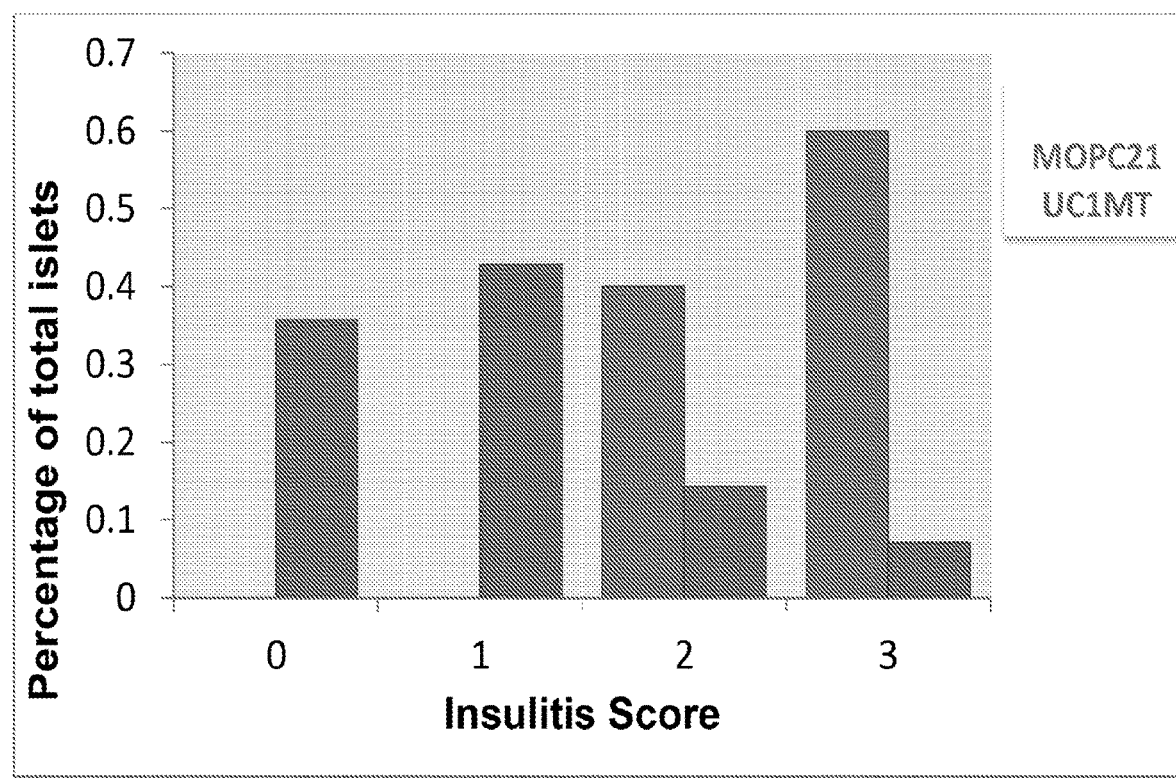
FIG. 9. Graph showing effects of MOPC21 or UC1MT on infiltration of inflammatory cells into the islets of Langerhans (insulinitis).

We used female NOD (non-obese diabetic) mouse for our type 1 DM prevention study because the NOD mouse has been found to spontaneously develops type 1 DM since it was described in 1980. Its pathogenic events begin at least as early as 3 weeks after birth with presentation of islet antigens in the pancreatic lymph nodes. Insulitis with first APC then lymphocytes, begins at about 4-6 weeks of age and steadily progresses over the next 15 weeks. Frank diabetes as BS>250 mg/dl begins between 18 and 20 weeks. Also, the incidence of spontaneous diabetes in the NOD mouse is 60-80% in females and 20-30% in males. Thus, we decided to divide the NOD mice into 3 groups (10 animals per treatment group): (1) treatment with PBS for negative control, (2) therapy with non-specific IgG at 0.1 mg/ml, MOPC as isotype control, and (3) daily intraperitoneal injection of 0.1 mg/ml of UCIMT per mouse, in order to investigate the potential role of anti-MT monoclonal antibody in T1 DM. Each group received their assigned treatment beginning at 5 weeks of age. The total therapeutic course was 2 weeks. Blood glucose levels were checked weekly, and mice that had blood glucose of greater than 250 mg/dl for 2 weeks were sacrificed. The rest of the NOD mice without diabetes were sacrificed at the age of 30 weeks. As shown in FIG. 7 and FIG. 8, anti-MT antibody treatment resulted in a remarkable alleviation of glucose intolerance in mice treated with high fat diet compared to isotype control MOPC21 or PBS vehicle control. UC1MT also led to a significant reduction in insulitis (i.e.: infiltration on inflammatory cells into the pancreatic islets of Langerhans) (FIG. 9).

We claim:

1. A composition, comprising:
    (a) an anti-metallothionein antibody or a fragment thereof which specifically binds to extracellular human metallothionein (MT); and
    (b) a pancreatic cell targeting moiety linked to the inhibitor of extracellular human MT.

2. The composition of claim 1, wherein the anti-MT antibody or an antigen-binding fragment thereof comprises a monoclonal antibody or an antigen binding fragment thereof.

3. The composition of claim 1, wherein the anti-MT antibody comprises a humanized anti-MT antibody, or an antigen binding fragment thereof.

4. The composition of claim 1, wherein the cell targeting moiety is glucagon-like peptide-1 (GLP-1).

5. The composition of claim 1, wherein the anti-metallothionein antibody or fragment thereof and the cell targeting moiety are expressed as a recombinant fusion polypeptide.

6. A pharmaceutical composition comprising:
    (a) the composition of claim 1; and
    (b) a pharmaceutically acceptable carrier.

7. The composition of claim 1, wherein the cell targeting moiety is peptide YY (PYY).

8. The composition of claim 1, wherein the cell targeting moiety is neuropeptide Y (NPY).

9. The composition of claim 1, wherein the cell targeting moiety is pancreatic peptide (PPY).

10. The composition of claim 1, wherein the cell targeting moiety is exendin-4.

* * * * *

SEQUENCE LISTING

<160> NUMBER OF SEQ ID NOS: 15

<210> SEQ ID NO 1
<211> LENGTH: 61
<212> TYPE: PRT
<213> ORGANISM: Homo sapiens

<400> SEQUENCE: 1

Met Asp Pro Asn Cys Ser Cys Ala Thr Gly Gly Ser Cys Thr Cys Thr
1               5                   10                  15

Gly Ser Cys Lys Cys Lys Glu Cys Lys Cys Thr Ser Cys Lys Lys Ser
            20                  25                  30

Cys Cys Ser Cys Cys Pro Met Ser Cys Ala Lys Cys Ala Gln Gly Cys
        35                  40                  45

Ile Cys Lys Gly Ala Ser Glu Lys Cys Ser Cys Cys Ala
    50                  55                  60

<210> SEQ ID NO 2
<211> LENGTH: 61
<212> TYPE: PRT
<213> ORGANISM: Homo sapiens

<400> SEQUENCE: 2

Met Asp Pro Asn Cys Ser Cys Thr Thr Gly Gly Ser Cys Ala Cys Ala
1               5                   10                  15

Gly Ser Cys Lys Cys Lys Glu Cys Cys Thr Ser Cys Lys Lys Cys
                20                  25                  30

Cys Cys Ser Cys Cys Pro Val Gly Cys Ala Lys Cys Ala Gln Gly Cys
            35                  40                  45

Val Cys Lys Gly Ser Ser Glu Lys Cys Arg Cys Ala
    50                  55                  60

<210> SEQ ID NO 3
<211> LENGTH: 61
<212> TYPE: PRT
<213> ORGANISM: Homo sapiens

<400> SEQUENCE: 3

Met Asp Pro Asn Cys Ser Cys Ala Thr Gly Gly Ser Cys Thr Cys Ala
1               5                   10                  15

Gly Ser Cys Lys Cys Lys Glu Cys Lys Cys Thr Ser Cys Lys Lys Ser
                20                  25                  30

Cys Cys Ser Cys Cys Pro Val Gly Cys Ala Lys Cys Ala Gln Gly Cys
            35                  40                  45

Val Cys Lys Gly Ala Ser Glu Lys Cys Ser Cys Ala
    50                  55                  60

<210> SEQ ID NO 4
<211> LENGTH: 61
<212> TYPE: PRT
<213> ORGANISM: Homo sapiens

<400> SEQUENCE: 4

Met Asp Pro Asn Cys Ser Cys Ala Ala Gly Val Ser Cys Thr Cys Ala
1               5                   10                  15

Gly Ser Cys Lys Cys Lys Glu Cys Lys Cys Thr Ser Cys Lys Lys Ser
                20                  25                  30

Cys Cys Ser Cys Cys Pro Val Gly Cys Ser Lys Cys Ala Gln Gly Cys
            35                  40                  45

Val Cys Lys Gly Ala Ser Glu Lys Cys Ser Cys Asp
    50                  55                  60

<210> SEQ ID NO 5
<211> LENGTH: 62
<212> TYPE: PRT
<213> ORGANISM: Homo sapiens

<400> SEQUENCE: 5

Met Asp Pro Asn Cys Ser Cys Ala Ala Gly Val Ser Cys Thr Cys
1               5                   10              15

Ala Ser Ser Cys Lys Cys Lys Glu Cys Lys Cys Thr Ser Cys Lys Lys
                20                  25                  30

Ser Cys Cys Ser Cys Cys Pro Val Gly Cys Ala Lys Cys Ala Gln Gly
            35                  40                  45

Cys Ile Cys Lys Gly Ala Ser Glu Lys Cys Ser Cys Ala
    50                  55                  60

<210> SEQ ID NO 6
<211> LENGTH: 61
<212> TYPE: PRT
<213> ORGANISM: Homo sapiens

<400> SEQUENCE: 6

Met Asp Pro Asn Cys Ser Cys Ala Ala Gly Asp Ser Cys Thr Cys Ala
1               5                   10                  15

Gly Ser Cys Lys Cys Lys Glu Cys Lys Cys Thr Ser Cys Lys Lys Ser
                20                  25                  30

Cys Cys Ser Cys Cys Pro Val Gly Cys Ala Lys Cys Ala Gln Gly Cys
            35                  40                  45

Ile Cys Lys Gly Ala Ser Asp Lys Cys Ser Cys Ala
    50                  55                  60

<210> SEQ ID NO 7
<211> LENGTH: 68
<212> TYPE: PRT
<213> ORGANISM: Homo sapiens

<400> SEQUENCE: 7

Met Asp Pro Glu Thr Cys Pro Cys Pro Ser Gly Gly Ser Cys Thr Cys
1               5                   10                  15

Ala Asp Ser Cys Lys Cys Glu Gly Cys Lys Cys Thr Ser Cys Lys Lys
                20                  25                  30

Ser Cys Cys Ser Cys Cys Pro Ala Glu Cys Glu Lys Cys Ala Lys Asp
            35                  40                  45

Cys Val Cys Lys Gly Gly Glu Ala Ala Glu Ala Glu Ala Glu Lys Cys
        50                  55                  60

Ser Cys Cys Gln
65

<210> SEQ ID NO 8
<211> LENGTH: 62
<212> TYPE: PRT
<213> ORGANISM: Homo sapiens

<400> SEQUENCE: 8

Met Asp Pro Arg Glu Cys Val Cys Met Ser Gly Gly Ile Cys Met Cys
1               5                   10                  15

Gly Asp Asn Cys Lys Cys Thr Thr Cys Asn Cys Lys Thr Tyr Trp Lys
                20                  25                  30

Ser Cys Cys Pro Cys Cys Pro Pro Gly Cys Ala Lys Cys Ala Arg Gly
            35                  40                  45

Cys Ile Cys Lys Gly Gly Ser Asp Lys Cys Ser Cys Cys Pro
        50                  55                  60

<210> SEQ ID NO 9
<211> LENGTH: 37
<212> TYPE: PRT
<213> ORGANISM: Artificial Sequence
<220> FEATURE:
<223> OTHER INFORMATION: Synthetic

<400> SEQUENCE: 9

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
                20                  25                  30

Val Lys Gly Arg Gly
                35

<210> SEQ ID NO 10
<211> LENGTH: 33

```
<212> TYPE: PRT
<213> ORGANISM: Artificial Sequence
<220> FEATURE:
<223> OTHER INFORMATION: Synthetic

<400> SEQUENCE: 10

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
                20                  25                  30

Asp

<210> SEQ ID NO 11
<211> LENGTH: 95
<212> TYPE: PRT
<213> ORGANISM: Artificial Sequence
<220> FEATURE:
<223> OTHER INFORMATION: Synthetic

<400> SEQUENCE: 11

Met Ala Ala Ala Arg Leu Cys Leu Ser Leu Leu Leu Ser Thr Cys
1               5                   10                  15

Val Ala Leu Leu Leu Gln Pro Leu Leu Gly Ala Gln Gly Ala Pro Leu
                20                  25                  30

Glu Pro Val Tyr Pro Gly Asp Asn Ala Thr Pro Glu Gln Met Ala Gln
                35                  40                  45

Tyr Ala Ala Asp Leu Arg Arg Tyr Ile Asn Met Leu Thr Arg Pro Arg
                50                  55                  60

Tyr Gly Lys Arg His Lys Glu Asp Thr Leu Ala Phe Ser Glu Trp Gly
65                  70                  75                  80

Ser Pro His Ala Ala Val Pro Arg Glu Leu Ser Pro Leu Asp Leu
                85                  90                  95

<210> SEQ ID NO 12
<211> LENGTH: 97
<212> TYPE: PRT
<213> ORGANISM: Artificial Sequence
<220> FEATURE:
<223> OTHER INFORMATION: Synthetic

<400> SEQUENCE: 12

Met Leu Gly Asn Lys Arg Leu Gly Leu Ser Gly Leu Thr Leu Ala Leu
1               5                   10                  15

Ser Leu Leu Val Cys Leu Gly Ala Leu Ala Glu Ala Tyr Pro Ser Lys
                20                  25                  30

Pro Asp Asn Pro Gly Glu Asp Ala Pro Ala Glu Asp Met Ala Arg Tyr
                35                  40                  45

Tyr Ser Ala Leu Arg His Tyr Ile Asn Leu Ile Thr Arg Gln Arg Tyr
                50                  55                  60

Gly Lys Arg Ser Ser Pro Glu Thr Leu Ile Ser Asp Leu Leu Met Arg
65                  70                  75                  80

Glu Ser Thr Glu Asn Val Pro Arg Thr Arg Leu Glu Asp Pro Ala Met
                85                  90                  95

Trp

<210> SEQ ID NO 13
<211> LENGTH: 97
<212> TYPE: PRT
<213> ORGANISM: Artificial Sequence
<220> FEATURE:
```

```
<223> OTHER INFORMATION: Synthetic

<400> SEQUENCE: 13

Met Val Phe Val Arg Arg Pro Trp Pro Ala Leu Thr Thr Val Leu Leu
1               5                   10                  15

Ala Leu Leu Val Cys Leu Gly Ala Leu Val Asp Ala Tyr Pro Ile Lys
            20                  25                  30

Pro Glu Ala Pro Gly Glu Asp Ala Ser Pro Glu Glu Leu Asn Arg Tyr
        35                  40                  45

Tyr Ala Ser Leu Arg His Tyr Leu Asn Leu Val Thr Arg Gln Arg Tyr
    50                  55                  60

Gly Lys Arg Asp Gly Pro Asp Thr Leu Leu Ser Lys Thr Phe Phe Pro
65                  70                  75                  80

Asp Gly Glu Asp Arg Pro Val Arg Ser Arg Ser Glu Gly Pro Asp Leu
                85                  90                  95

Trp

<210> SEQ ID NO 14
<211> LENGTH: 87
<212> TYPE: PRT
<213> ORGANISM: Artificial Sequence
<220> FEATURE:
<223> OTHER INFORMATION: Synthetic

<400> SEQUENCE: 14

Met Lys Ile Ile Leu Trp Leu Cys Val Phe Gly Leu Phe Leu Ala Thr
1               5                   10                  15

Leu Phe Pro Ile Ser Trp Gln Met Pro Val Glu Ser Gly Leu Ser Ser
            20                  25                  30

Glu Asp Ser Ala Ser Ser Glu Ser Phe Ala Ser Lys Ile Lys Arg His
        35                  40                  45

Gly Glu Gly Thr Phe Thr Ser Asp Leu Ser Lys Gln Met Glu Glu Glu
    50                  55                  60

Ala Val Arg Leu Phe Ile Glu Trp Leu Lys Asn Gly Gly Pro Ser Ser
65                  70                  75                  80

Gly Ala Pro Pro Pro Ser Gly
                85

<210> SEQ ID NO 15
<211> LENGTH: 5
<212> TYPE: PRT
<213> ORGANISM: Artificial Sequence
<220> FEATURE:
<223> OTHER INFORMATION: Synthetic

<400> SEQUENCE: 15

Lys Leu Lys Gln Pro
1               5
```